United States Patent [19]
Meyer

[11] Patent Number: 6,106,559
[45] Date of Patent: Aug. 22, 2000

[54] SOCKET COUPLER FOR A PROSTHETIC LIMB

[76] Inventor: Dennis E. Meyer, 11150 Baltimore-Phillipsburg, Brookville, Ohio 45309

[21] Appl. No.: 09/275,987

[22] Filed: Mar. 25, 1999

[51] Int. Cl.[7] .................................................. A61F 2/80
[52] U.S. Cl. .............................................. 623/33; 623/38
[58] Field of Search .......................................... 623/33–38

[56] References Cited

U.S. PATENT DOCUMENTS

| | | | |
|---|---|---|---|
| 5,226,918 | 7/1993 | Silagy et al. | 623/32 |
| 5,376,129 | 12/1994 | Faulkner et al. | |
| 5,662,715 | 9/1997 | Slemker. | |
| 5,702,489 | 12/1997 | Slemker. | |

*Primary Examiner*—David H. Willse
*Attorney, Agent, or Firm*—Jacox, Meckstroth & Jenkins

[57] ABSTRACT

The stump of an amputee's limb receives a sleeve which is inserted into a formed plastic socket, and a locking stud with axially spaced peripheral grooves projects from the sleeve. A coupler is mounted within the bottom of the socket and has a top conical surface with inclined tapering guide grooves which extend to a tubular center bushing slidable within a tubular fitting. A set of circumferentially spaced locking balls are confined within holes in the bushing and move between locking positions projecting into one of the grooves of the locking stud and retracted release positions in response to axial movement of the bushing within the fitting. An actuator stem projects laterally from the coupler and has cam surfaces effective to rotate a pair of actuating pins to shift the bushing and release the locking balls in response to axial or rotary movement of the actuator stem. The actuator stem may also be rotated to a position where the actuator stem is locked against axial movement and accidental release of the locking stud. The actuator stem also has a gripping knob which provides an indication of the stem's rotational position.

20 Claims, 5 Drawing Sheets

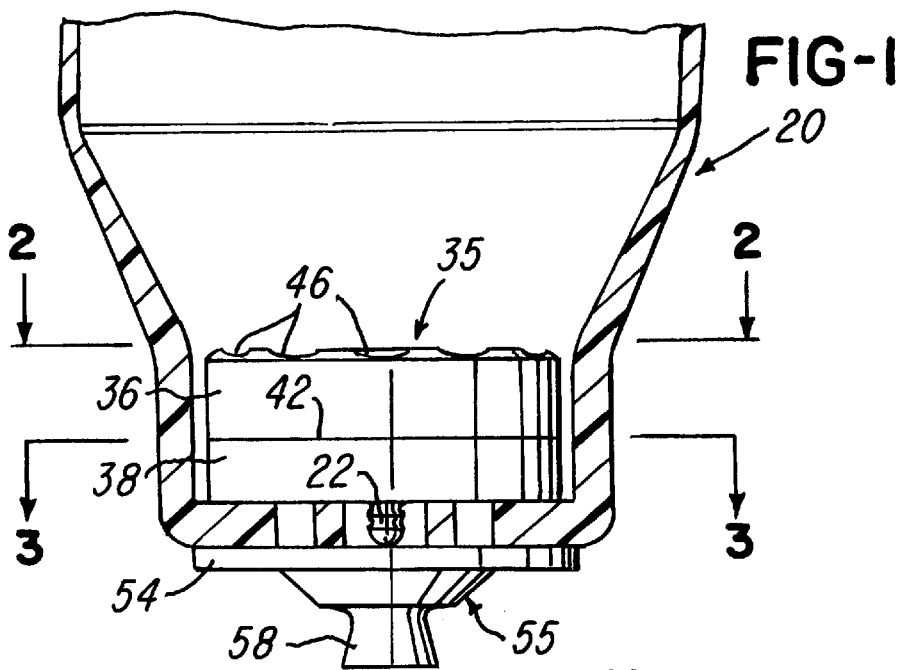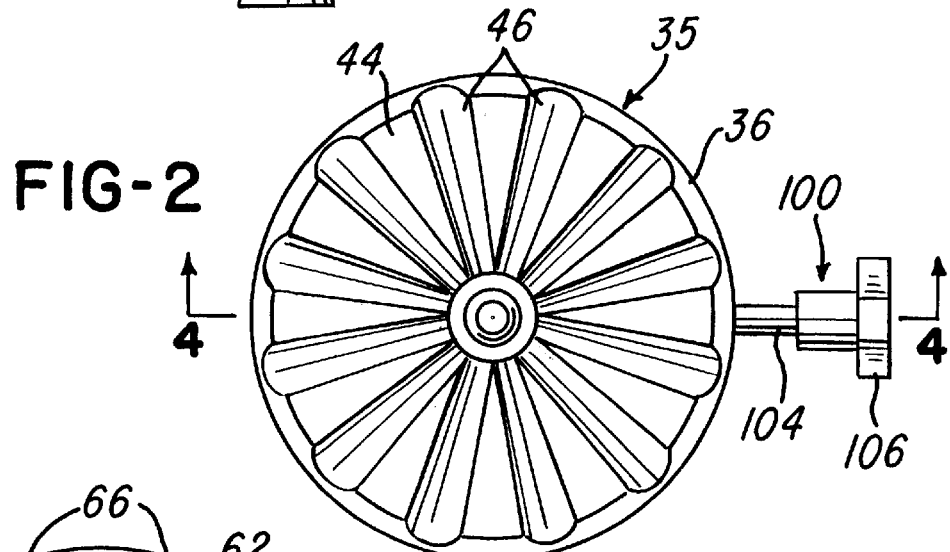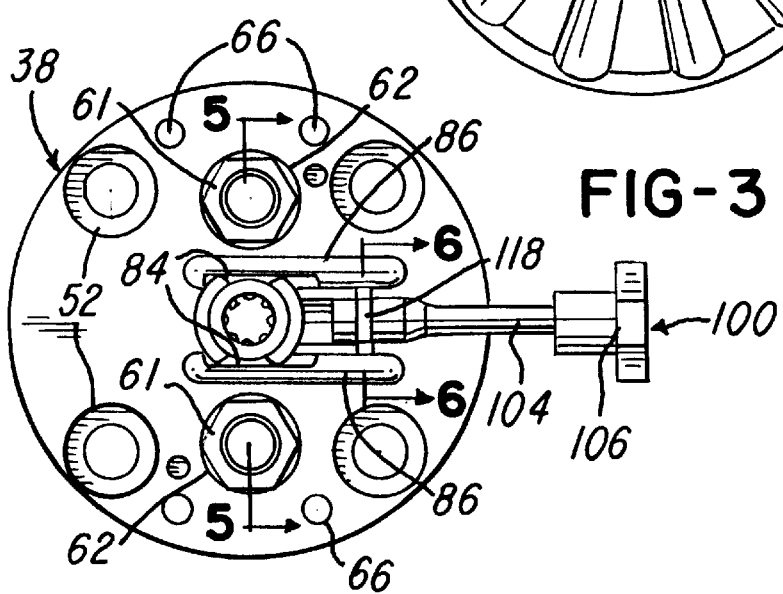

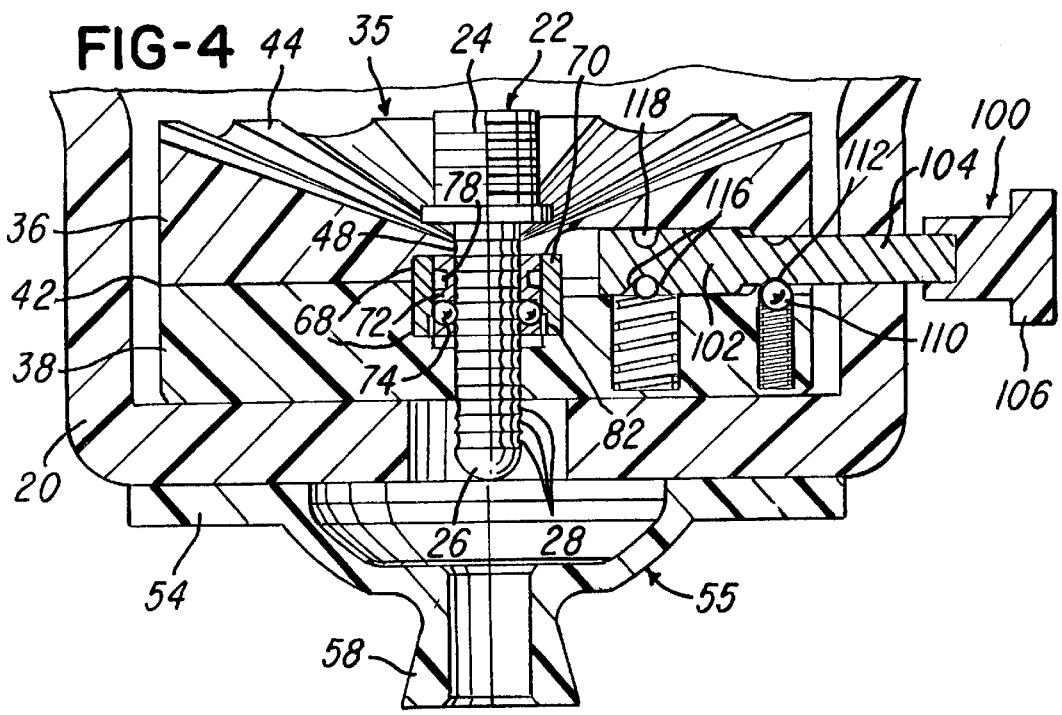
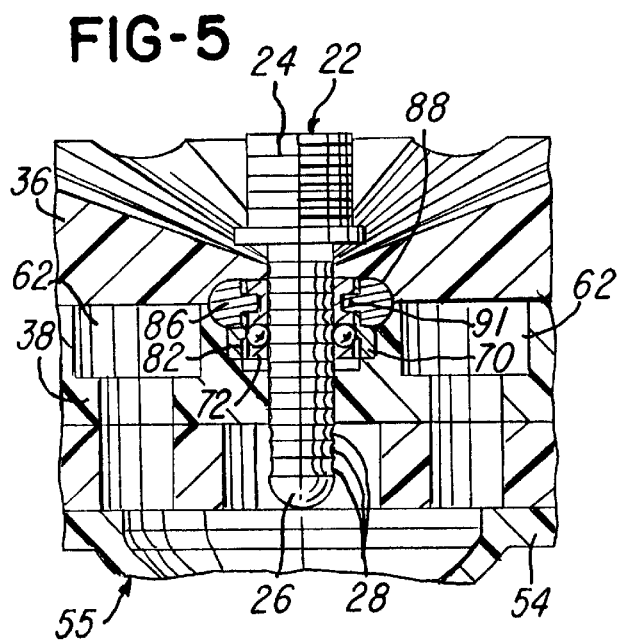
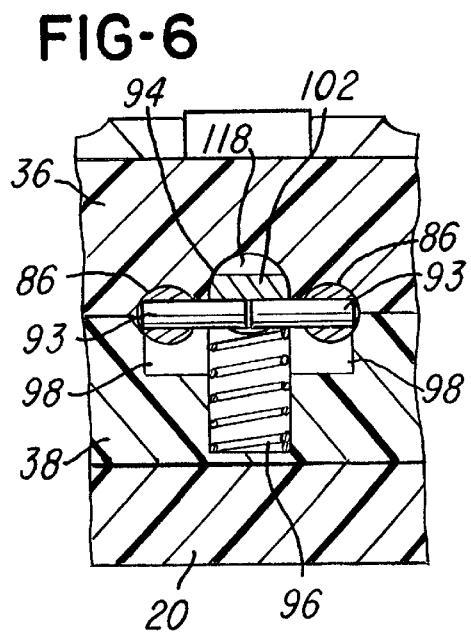

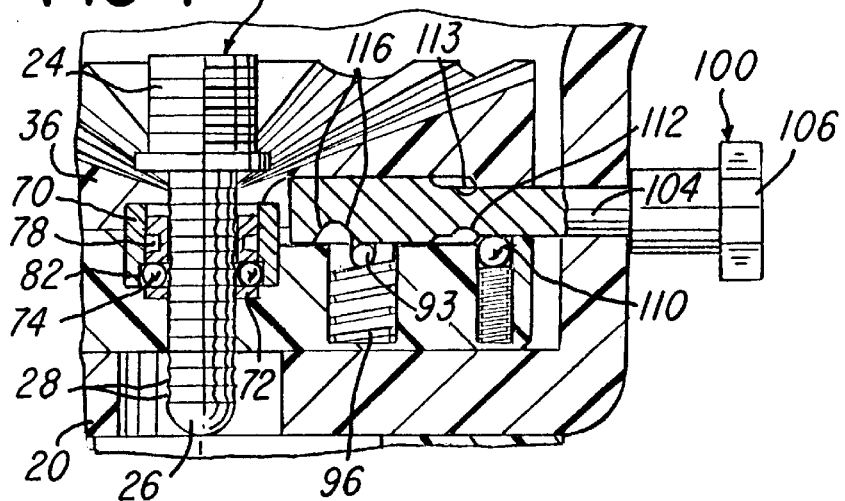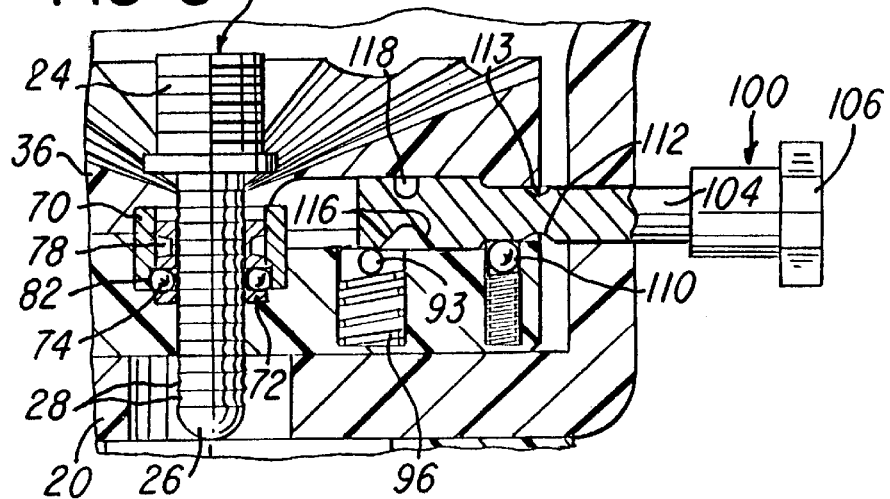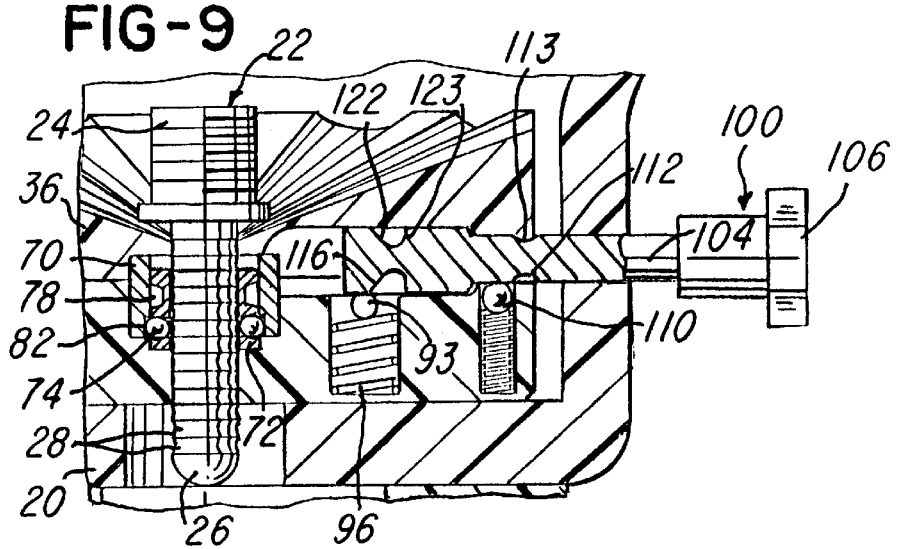

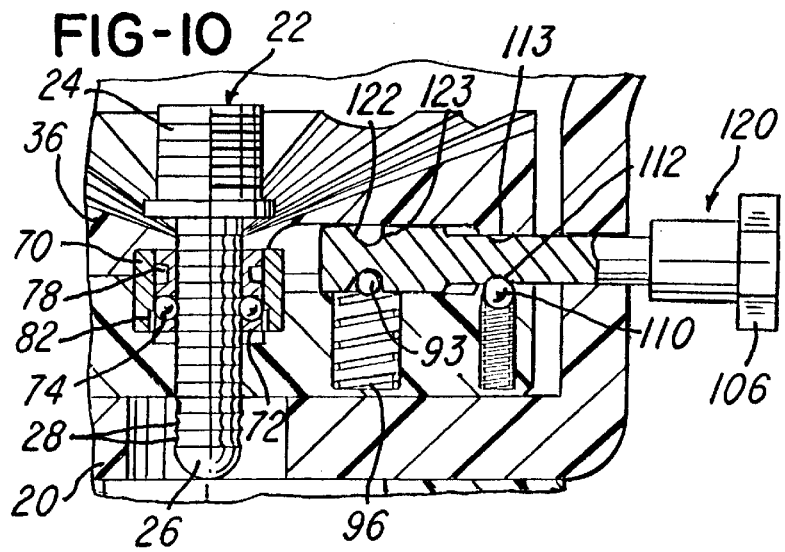
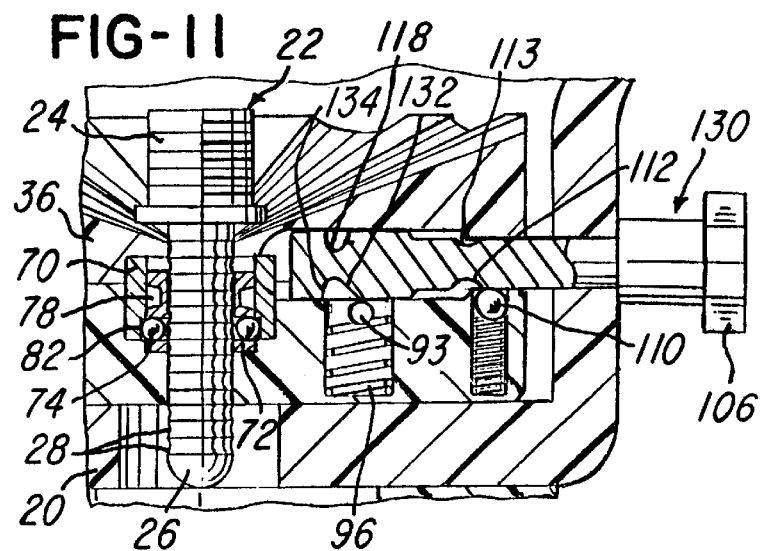
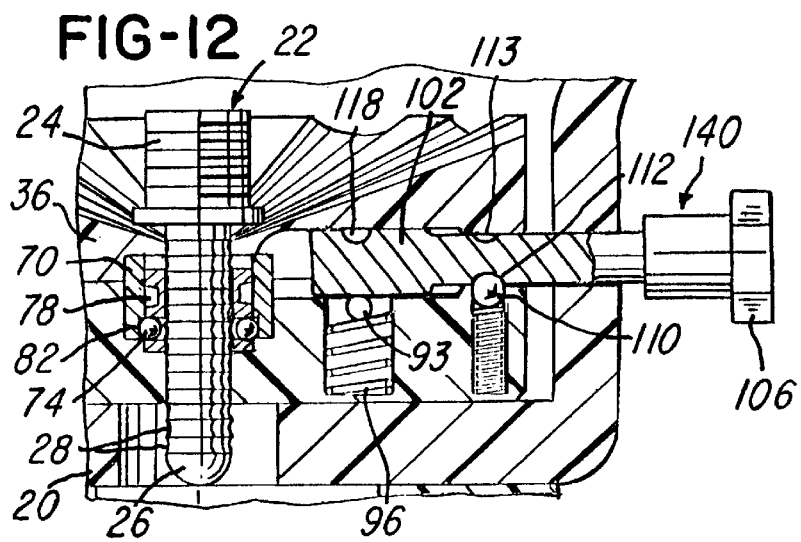

SOCKET COUPLER FOR A PROSTHETIC LIMB

BACKGROUND OF THE INVENTION

This invention relates to an improved coupler for releasably connecting a prosthetic device such as an artificial leg or arm to a sleeve which receives the stump of an amputee's limb and has a projecting locking stud, for example, as disclosed in U.S. Pat. No. 5,376,129. As illustrated in FIGS. 9–11 of this patent, it is known to have an attachment device or coupler which uses a retractable release stem having a wedge-shaped inner end portion or pawl for engaging one of a plurality of grooves formed within the locking stud projecting from the sleeve. This general form of attachment device or coupler is made by the inventor of the present invention and sold by Prosthetic Design, Inc. of Clayton, Ohio under the trademark PDI. This company also sells another coupler manufactured by the inventor of the present invention and wherein the pawl is connected by a pivotal lever to the release stem so that the pawl is retracted to a released position when the stem is pushed inwardly. It is also known to retain the sleeve within the socket by means of a suction coupler, for example, of the type shown in U.S. Pat. No. 5,662,715 and U.S. Pat. No. 5,702,489 which disclose couplers made by the inventor of the present invention for the Assignee of the patents.

It has been found desirable to provide a prosthetic attachment device or coupler which provides the amputee user with a means for locking the coupler so that it may not be accidentally released, for example, by accidentally pushing or pulling the actuator stem. It has also been found desirable to provide a coupler which may be easily converted and assembled to provide an actuator stem which may be pushed to release and/or pulled to release and/or rotated to release the locking stud from the coupler. In addition, the coupler should provide for conveniently receiving the locking stud projecting from the sleeve, and for a positive and dependable lock with the locking stud.

SUMMARY OF THE INVENTION

The present invention is directed to an improved coupler for releasably connecting a prosthetic device such as an artificial leg to a sleeve configured to receive the stump of an amputee's limb and which provides all of the desirable advantages mentioned above. In accordance with a preferred embodiment of the invention, the sleeve has a projecting locking stud with a series of axially spaced circumferential grooves. The attachment device or coupler includes a generally cylindrical body having an upper section and a lower section each formed or molded of metal or a rigid plastics material. The lower section is secured to the bottom wall of the socket by a set of four screws, and another set of screws secure the upper and lower body sections together.

The top surface of the upper section has a generally conical surface interrupted by a circumferentially spaced tapered guide grooves which converge downwardly for guiding the end of the locking stud into a tubular bushing confined between the body sections. The bushing retains a series of peripherally spaced balls which are retained in the bushing by a surrounding tubular fitting which also provides for axial movement of the tubular bushing for shifting the balls between locking positions engaging one of the grooves in the locking stud and retracted released positions. Axial movement of the bushing is produced by rotation of a pair of actuating pins spaced to engage opposite sides of the bushing.

The actuating pins have cross pins which are spring biased against cam surfaces and locking surfaces on an actuator stem extending radially outwardly from the coupler through a clearance hole within the socket. The actuator stem is provided with various cam surfaces and locking surfaces which provide for locking the stem against axial movement and cam surfaces which provide for either push to release and/or pull to release and/or rotation to release in addition to rotation to a locking position. The actuator stem also has an outer gripping knob which provides the user with both a non-visual and a visual indication of each position of the actuator stem.

Other features and advantages of the invention will be apparent from the following description, the accompanying drawings and the appended claims.

BRIEF DESCRIPTION OF THE DRAWINGS

FIG. 1 is an elevational view of a coupler constructed in accordance with the invention and installed within a surrounding socket shown in axial section;

FIG. 2 is a top view of the coupler as taken generally on the line 2—2 of FIG. 1, but without the socket;

FIG. 3 is a plan view of the bottom section of the coupler body with the top section removed, taken generally on the line 3—3 of FIG. 1, but without the socket;

FIG. 4 is an enlarged section of the coupler as taken generally on the line 4—4 of FIG. 2 and with the socket and mounting bracket also shown in axial section;

FIG. 5 is an enlarged fragmentary section taken generally on the line 5—5 of FIG. 3;

FIG. 6 is an enlarged fragmentary section taken generally on the line 6—6 of FIG. 3;

FIGS. 7–13 are fragmentary sections of the coupler and illustrating the locked, released and unlocked positions of different actuating stems constructed in accordance with the invention.

DESCRIPTION OF THE PREFERRED EMBODIMENTS

Figure 13:
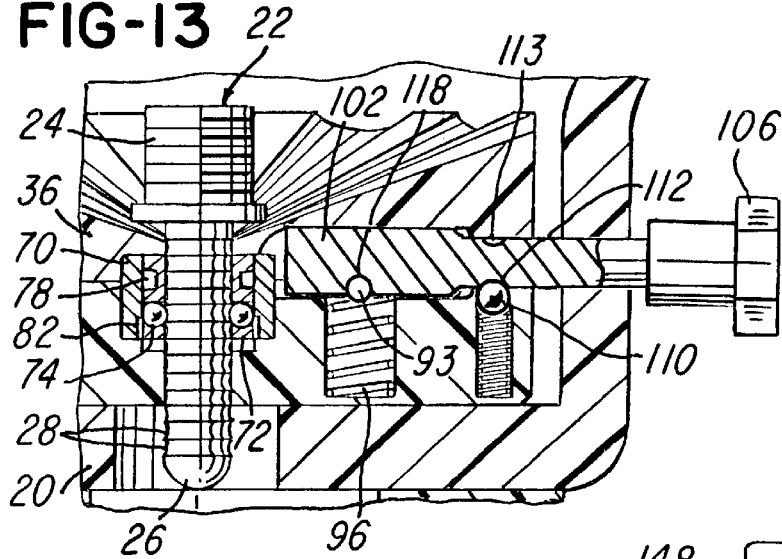

A hollow cup-like socket 20 (FIG. 1) is molded of a heat-formable rigid plastics material and is constructed similar to the socket 500 disclosed in FIG. 11 of above-mentioned U.S. Pat. No. 5,376,129, the disclosure of which is incorporated by reference. The socket 20 is adapted to receive a semi-flexible sleeve (not shown), such as the sleeve 410 disclosed in FIG. 11 of U.S. Pat. No. 5,376,129, and from which projects or depends a metal locking stud 22 having a threaded upper end portion 24 attached to a boss on the bottom of the sleeve. The locking stud 22 has a lower shank portion 26 with a series of axially spaced circumferential grooves 28 each having a curved configuration in axial cross-section.

In accordance with the present invention, the locking stud 22 is releasably connected or locked to the socket 20 by a coupler 35 which is formed with an upper body section 36 and a lower body section 38 each formed of metal or molded of a rigid plastic material and secured together by screws at an interface 42. The upper section 36 has a generally conical upper surface 44 (FIG. 2) with circumferentially spaced and spoke-like inclined stud guiding grooves 46 which taper inwardly and downwardly to a center hole 48 (FIG. 4) within the top section 36.

The lower body section 38 of the coupler 35 has a set of four counterbore holes 52 (FIG. 3) which receive corresponding nuts (not shown) for receiving a set of threaded fasteners or screws which extend upwardly through aligned holes within the base of the socket and a flange 54 (FIG. 4) of an annular attachment bracket 55. The bracket 55 has a tapered annular lower portion 58 which is adapted to be coupled to the shaft of an artificial limb, for example, as disclosed in FIG. 11 of above-mentioned U.S. Pat. No. 5,376,129. The nuts within the holes 52 may also receive flat head screws (not shown) for securing only the socket 20 to the coupler 35 when a different form of connector bracket is used in place of the bracket 55. When an artificial limb shaft is attached or connected as shown in above-mentioned U.S. Pat. No. 5,662,715, a pair of nuts 61 (FIG. 3) are recessed within counterbore holes 62 for receiving a pair of attachment screws such as the screws or bolts disclosed in FIG. 3 of above-mentioned U.S. Pat. No. 5,662,715.

As mentioned above, the upper body section 36 and the lower body section 38 of the coupler 35 are secured together by a set of four screws (not shown) which extend upwardly within four counterbore holes 66 (FIG. 3) within the lower section 38 and are threaded into corresponding holes (not shown) within the bottom portion of the upper section 36. A cylindrical bore or cavity 68 (FIG. 4) is formed within the center portion of the coupler sections 36 and 38 and receives a tubular metal fitting 70 which supports a tubular bushing 72 for axial sliding movement. The bushing 72 has a plurality of eight peripherally spaced holes which receive corresponding steel balls 74. The balls are adapted to project into one of the grooves 28 within the locking stud 22, as shown in FIG. 4.

The bushing 72 also has an annular groove 78 (FIG. 4), and the surrounding supporting fitting 70 has a lower portion with an annular recess 82. When the bushing 72 moves downwardly within the fitting 70, the balls 74 are free to shift radially outwardly in their corresponding holes into the cavity 82 to released positions, thereby releasing the balls from locking engagement with the locking stud 22. Referring again to FIG. 3, the upper portion of the tubular fitting 70 has diametrically opposed notches or recesses 84 which receive a pair of parallel spaced actuating pins 86 supported for rotation within corresponding mating cavities 88 (FIGS. 5 and 6) formed within the coupler sections 36 and 38 at the interface 42. Each of the pins 86 has a rib 91 which projects into the groove 78 within the fitting 70, as shown in FIG. 5. Thus rotation of the actuating pins 86 in opposite directions is effective to move the bushing 72 axially within the fitting 70 for moving the balls 74 between stud locking positions (FIG. 4) and stud released positions (FIG. 7).

Each of the actuating pins 86 supports a cross pin 93 (FIG. 6), and the cross pins 93 project inwardly into a cylindrical cavity or bore 94. The actuating pins 86 and cross pins 93 are normally held in stud locking positions (FIGS. 4 and 6) by a compression spring 96 retained within a cylindrical cavity 97 within the bottom coupler section 38. When the adjacent and opposing end portions of the cross pins 93 are pressed downwardly to compress the spring 96, the pins 93 are free to move within corresponding slots 98 in order to rotate the actuating pins 86 to move the bushing 72 and balls 74 from their stud locking positions (FIG. 4) to their stud released positions (FIG. 7).

The simultaneous rotation of the actuating pins 86 and corresponding cross pins 93 for moving the bushing 72 and balls 74 to their released positions is produced by movement of an actuator pin or stem 100 (FIG. 4). The stem 100 has a cylindrical inner end portion 102 and a smaller diameter outer end portion 104 attached to an actuator knob 106. The cylindrical portions 102 and 104 are supported for both rotational and axial movement within corresponding cylindrical bores formed within the mating coupler sections 36 and 38, and a spring biased detent ball 110 seats within one of three part-spherical cavities 112 formed within a partial circumferential groove 113 (FIG. 8) within the stem portion 104 to provide the operator with a feel or indication as to the position of the actuator stem 100.

The coupler 35 is adapted to receive a variety of selectable different actuator stems 100, depending upon the mode of desired release of the sleeve locking stud 22. In one embodiment, the inner cylindrical portion 102 of the actuator stem 100 has a V-shaped groove formed by converging cam surfaces 116 (FIGS. 4, 7, 8, 14 and 15). The groove extends laterally across the stem portion 102 and is intersected by a U-shaped locking groove 118. When the actuator stem 100 is used, the locking stud 22 may be released by either pushing or pulling the actuator stem 100 for rotating the actuating pins 86 and corresponding cross pins 93, as shown in FIGS. 7 and 8. However, when it is desired to lock the actuator stem 100 from axial movement, the stem is rotated until the cross pins 93 are received within the locking groove 118, as shown in FIG. 13, so that the locking stud 22 may not be accidentally released by pushing or pulling the actuator stem 100.

FIGS. 9 and 10 illustrate an actuator stem 120 which is constructed to provide release of the locking stud 22 only by pulling the actuator stem 120 from its stud locking position (FIG. 10) to the stud release position (FIG. 9). This is accomplished by forming a cross groove with an incline cam surface 122 and a radial surface 123. Thus when the groove receives the cross pins 93 (FIG. 10), the cross pins 93 are cammed downwardly by the cam surface 122 to release the locking stud 22 when the actuator stem 120 is pulled outwardly. The actuator stem 120 may also be provided with a U-shaped locking groove or slot 118 if it is desired to rotate the actuator stem 120 to its locked position so that the locking stud 22 may not be released until the actuator stem 120 is rotated back to a position where the cam surface 122 may engage the cross pins 93.

FIG. 11 illustrates an actuator stem 130 which releases the locking stud 22 when the actuator stem 130 is pushed inwardly. That is, the cross pins 93 are received within a cross groove or slot defined by an incline cam surface 132 and a radial surface 134. The actuator stem 130 is also provided with a U-shaped locking slot 118 so that when the actuator stem 130 is pulled outwardly to a locking position for the locking stud 22, the actuator stem 130 may be rotated until the cross pins 93 move into the locking slot 118 which then prevents axial movement of the actuator stem 130 until the actuator stem is rotated back to a position with the cross pins 93 within the groove defined by the surfaces 132 and 134.

FIGS. 12 and 13 illustrate the use of an actuator stem 140 which has a U-shaped locking groove 118 for receiving the cross pins 93 (FIG. 13) to prevent any axial movement of the actuator stem 140. When the actuator stem 140 is rotated, the cross pins 93 are cammed downwardly by cam surfaces at the ends of the cross slot 118 for shifting the bushing 72 downwardly within the fitting 70 so that the balls 74 are cammed outwardly into the cavity or recess 82 when the locking stud 22 is pulled upwardly.

Figure 14:
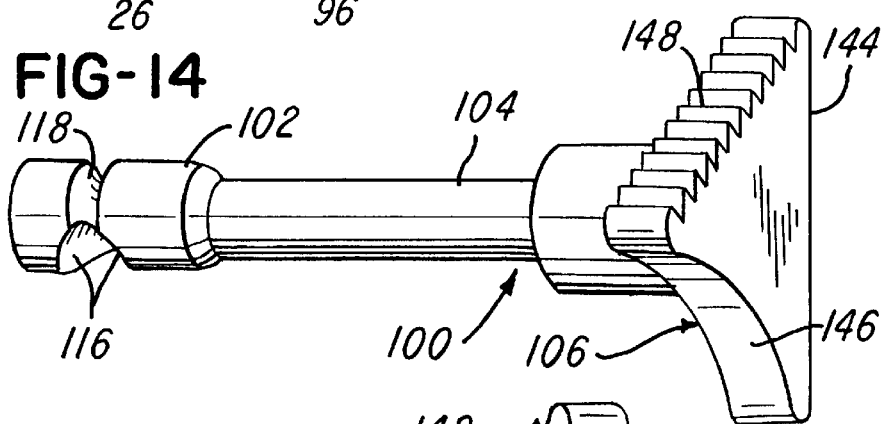
FIGS. 14–16 are perspective views of three different actuator stems used in the coupler body shown in FIGS. 7–13 according to the desired operating features.
Figure 15:
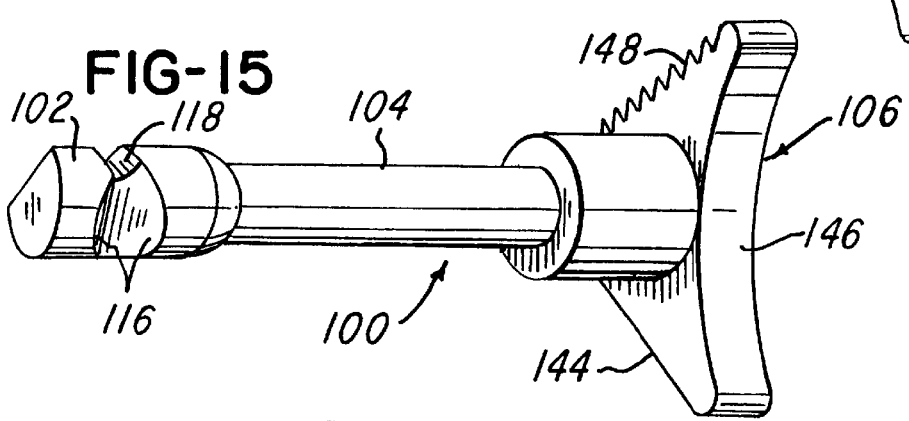
Figure 16:
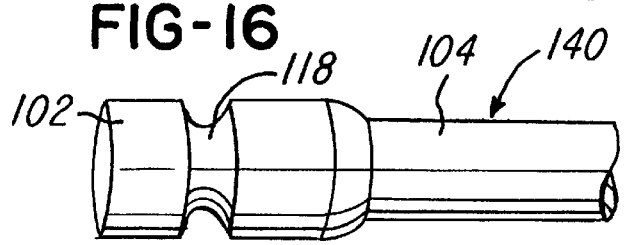

Whenever it is desired to provide a detent for an actuator stem in a particular locked or unlocked position, the stem portion 104 is provided with a part spherical cavity 112 for receiving the spring biased ball 110. Referring to FIGS. 14–16, preferably the knob 106 of the actuator stem 100 or 120 or 130 or 140 is provided with a generally triangular configuration with a flat surface 144, a curved surface 146 and a serrated surface 148. The surfaces provide a feel-type indication to the user of the rotational position of the actuator stem while the detent cavities 112 and circumferential groove 113 provide the user with an indication of the axial position of the actuator stem.

From the drawings and the above description, it is apparent that a coupler constructed in accordance with the present invention, provides desireable features and advantages. As one feature, the circumferentially spaced locking balls 74 within the tubular bushing 72 provide for a positive and high strength connection with a selected groove 28 within the locking stud 22 and with small pitch increments. It is also apparent that when the locking stud 22 is pressed downwardly into the bushing 72, the bushing shifts downwardly against the bias of the spring 96 until the balls 74 move outwardly to a released position within the cavity 82. Thus, the user detects a fine ratchet action when the locking stud 22 is inserted into the bushing 72 until the desired positive and firm connection is made between the stump receiving sleeve and the socket 20.

As another feature, the coupler releasing mechanism or actuator provides for rotating the actuator stem to a locking position which prevents release of the stud 22 until the actuator stem is rotated back to a releasing position. When the actuator stem is in its locked position, the stud 22 cannot be released by accidentally pushing or pulling on the knob of the actuator stem. By using different or modified actuator stems, it is apparent that the coupler may be provided with push to release and/or pull to release, or rotate to release, or rotate to lock for any of the various releasing positions. In addition, the non-uniform configuration of the knob 106 for the actuator stem provides a user who is unable to see the actuator stem with a feel as to the rotary position of the actuator stem. The grooves 46 within the top surface of the coupler provide a direct guide for the locking stud 22 into the bushing 72.

While the forms of coupler apparatus herein described constitute preferred embodiments of the invention, it is to be understood that the invention is not limited to these precise forms of apparatus, and that changes may be made therein without departing from the scope and spirit of the invention as defined in the appended claims.

What is claimed is:

1. A coupler for releasably connecting a prosthetic device to a sleeve having a projecting locking stud with the sleeve configured to receive the stump of a limb, said coupler comprising a body supporting a tubular bushing within a tubular fitting, said bushing confining a series of circumferentially spaced balls, said locking stud having a plurality of axially spaced circumferential grooves and adapted to extend into said bushing, said balls being moveable between locking positions projecting into one of said grooves of said locking stud and released positions retracted from said groove in response to relative axial movement between said bushing and said fitting, and an actuator connected to produce said relative axial movement between said bushing and said fitting to permit movement of said balls between said released and locking positions.

2. A coupler as defined in claim 1 wherein said actuator comprises an actuator stem projecting laterally of said body, said actuator stem supported by said body and connected to produce said relative axial movement between said bushing and said fitting in response to axial movement of said actuator stem, and said actuator stem having a locked position preventing axial movement of said actuator stem.

3. A coupler as defined in claim 1 wherein said actuator comprises a pair of parallel spaced generally cylindrical actuating pins supported for rotation on corresponding parallel axes and receiving said bushing therebetween, said actuating pins having portions engaging said bushing and effective to move said bushing axially within said fitting in response to rotation of said actuating pins.

4. A coupler as defined in claim 3 wherein said actuator includes an elongated actuator stem supported for movement by said body and projecting laterally of said body, and said actuating pins include spring biased cross pins engaging a cam surface on said actuator stem for producing rotation of said actuating pins in response to movement of said actuator stem.

5. A coupler as defined in claim 4 wherein said bushing, said actuating pins and said actuator stem are confined within corresponding mating cavities within first and second sections of said coupler body.

6. A coupler as defined in claim 1 wherein said actuator comprises an actuator stem projecting laterally of said body, means for producing said relative axial movement between said bushing and said fitting in response to movement of said actuator stem, and said actuator stem having a releasable locked position preventing axial movement of said actuator stem.

7. A coupler as defined in claim 6 wherein said actuator stem has a cross slot defined by at least one inclined cam surface.

8. A coupler as defined in claim 6 wherein said actuator stem has a cross slot with a U-shape cross-sectional configuration to provide for rotating said actuator stem to a locked position preventing axial movement of said actuator stem.

9. A coupler as defined in claim 1 wherein said bushing and said balls move axially within said fitting in response to insertion of said locking stud into said bushing.

10. A coupler as defined in claim 1 wherein said grooves within said locking stud are immediately adjacent each other in a series to provide said grooves with a fine pitch.

11. A coupler as defined in claim 1 wherein said body has a top conical surface with circumferentially spaced guide grooves for directing said locking stud into said bushing.

12. A coupler for releasably connecting a prosthetic device to a sleeve having a projecting locking stud with the sleeve configured to receive the stump of a limb, said coupler comprising a body supporting a tubular bushing for axial movement within a tubular fitting, said bushing confining a series of circumferentially spaced balls, said locking stud having a plurality of axially spaced circumferential grooves and adapted to extend into said bushing, said balls being moveable between locking positions projecting into one of said grooves of said locking stud and released positions retracted from said groove in response to axial movement of said bushing within said fitting, an actuator connected to produce said axial movement of said bushing within said fitting to permit movement of said balls between said released and locking positions, said actuator including an actuator stem projecting laterally of said body, said actuator stem supported by said body and connected to produce said axial movement of said bushing within said fitting in response to axial movement of said actuator stem, and said actuator stem having a locked position preventing axial movement of said actuator stem.

13. A coupler as defined in claim 12 wherein said actuator comprises a pair of parallel spaced generally cylindrical actuating pins supported for rotation on corresponding parallel axes and receiving said bushing therebetween, said actuating pins having portions engaging said bushing and effective to move said bushing axially within said fitting in response to rotation of said actuating pins.

14. A coupler as defined in claim 13 wherein said actuating pins include spring biased cross pins positioned to engage a cam surface on said actuator stem for producing rotation of said actuating pins in response to movement of said actuator stem.

15. A coupler as defined in claim 14 wherein said bushing, said actuating pins and said actuator stem are confined within corresponding mating cavities within first and second sections of said coupler body.

16. A coupler as defined in claim 12 wherein said actuator stem has a cross slot defined by at least one inclined cam surface.

17. A coupler as defined in claim 12 wherein said actuator stem has a cross slot with a U-shape cross-sectional configuration to provide for rotating said actuator stem to a locked position preventing axial movement of said actuator stem.

18. A coupler as defined in claim 12 wherein said bushing and said balls are spring biased against axial movement within said fitting, and said bushing and said balls move axially within said fitting against said bias in response to insertion of said locking stud into said bushing.

19. A coupler as defined in claim 12 wherein said grooves within said locking stud are immediately adjacent each other in a series to provide said grooves with a fine pitch.

20. A coupler for releasably connecting a prosthetic device to a sleeve having a projecting locking stud with the sleeve configured to receive the stump of a limb, said coupler comprising a body supporting a tubular bushing, said locking stud having a plurality of axially spaced grooves and adapted to extend into said bushing, locking means moveable between a locking position projecting into one of said grooves of said locking stud and a released position retracted from said groove, an actuator stem projecting laterally of said body, said actuator stem supported by said body and connected to produce movement of said locking means from said locking position to said released position in response to axial movement of said actuator stem, and said actuator stem having a locked position preventing axial movement of said actuator stem.

* * * * *